United States Patent
Bertin-Mourot et al.

(10) Patent No.: US 7,430,049 B2
(45) Date of Patent: Sep. 30, 2008

(54) METHOD AND DEVICE FOR ANALYZING THE SURFACE OF A SUBSTRATE

(75) Inventors: Thomas Bertin-Mourot, Paris (FR); Jean-Pierre Douche, Le Plessis Brion (FR); Daniel Germond, Combs la Ville (FR); Paul-Henri Guering, Paris (FR); Yves Surrel, St. Etienne (FR)

(73) Assignee: Saint-Gobain Glass France, Courbevoie (FR)

( * ) Notice: Subject to any disclaimer, the term of this patent is extended or adjusted under 35 U.S.C. 154(b) by 261 days.

(21) Appl. No.: 10/432,269

(22) PCT Filed: Nov. 21, 2001
(Under 37 CFR 1.47)

(86) PCT No.: PCT/FR01/03658

§ 371 (c)(1),
(2), (4) Date: Apr. 5, 2004

(87) PCT Pub. No.: WO02/42715

PCT Pub. Date: May 30, 2002

(65) Prior Publication Data

US 2006/0050284 A1    Mar. 9, 2006

(30) Foreign Application Priority Data

Nov. 22, 2000    (FR) ........................ 00 15050

(51) Int. Cl.
    *G01B 11/24*    (2006.01)
(52) U.S. Cl. .................................... 356/605
(58) Field of Classification Search .............. 356/605
    See application file for complete search history.

(56) References Cited

U.S. PATENT DOCUMENTS

| | | | | |
|---|---|---|---|---|
| 3,619,023 | A | * 11/1971 | Brooks ........................ 359/3 |
| 4,102,578 | A | * 7/1978 | Suzuki et al. ................ 356/606 |
| 4,202,630 | A | * 5/1980 | Suzuki et al. ................ 356/606 |
| 4,653,104 | A | 3/1987 | Tamura | |
| 4,794,550 | A | * 12/1988 | Greivenkamp, Jr. ......... 702/167 |
| 5,202,749 | A | 4/1993 | Pfister | |

(Continued)

FOREIGN PATENT DOCUMENTS

DE    41 36 428    5/1993

(Continued)

OTHER PUBLICATIONS

Y Surrel: "Design of algorithms for phase 10 measurements by the use of phase stepping" Applied Optics, vol. 35, No. 1, pp. 51-60 1996.

*Primary Examiner*—Tarifur R. Chowdhury
*Assistant Examiner*—Isiaka O Akanbi
(74) *Attorney, Agent, or Firm*—Oblon, Spivak, McClelland, Maier & Neustadt, P.C.

(57) ABSTRACT

A process for scanning a surface of a substrate, which process takes at least one reflected image of at least one test pattern on the surface and extracts by digital processing local phases in two directions. Variations in local slopes are calculated by digital processing from the local phases to deduce therefrom variations in curvature or variations in altitude of the surface.

26 Claims, 2 Drawing Sheets

U.S. PATENT DOCUMENTS

Figure 1:
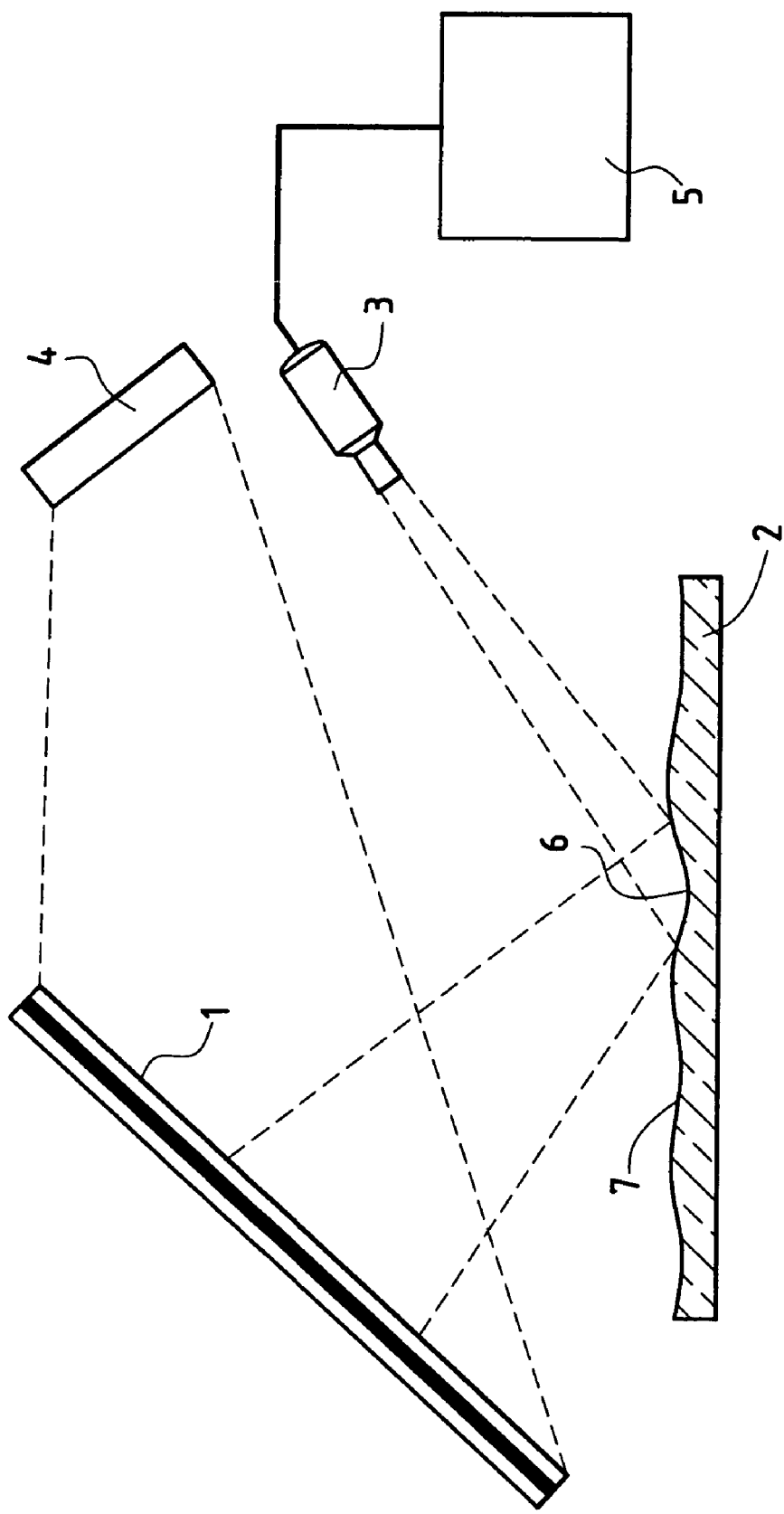

| | | |
|---|---|---|
| 5,307,152 A | 4/1994 | Boehnlein et al. |
| 5,608,529 A | 3/1997 | Hori |
| 5,714,832 A | 2/1998 | Liskow et al. |
| 5,835,223 A * | 11/1998 | Zwemer et al. ............. 356/600 |
| 5,875,029 A | 2/1999 | Cejna et al. |
| 5,969,819 A * | 10/1999 | Wang ......................... 356/600 |
| 5,995,224 A * | 11/1999 | de Groot ..................... 356/511 |
| 6,072,581 A * | 6/2000 | Stephenson et al. ......... 356/521 |

FOREIGN PATENT DOCUMENTS

| | | |
|---|---|---|
| DE | 195 19 520 | 12/1996 |
| EP | 0 551 955 | 7/1993 |
| EP | 0 924 494 | 6/1999 |
| EP | 1 065 498 | 1/2001 |
| WO | 98 55826 | 12/1998 |
| WO | 01 06210 | 1/2001 |

* cited by examiner

METHOD AND DEVICE FOR ANALYZING THE SURFACE OF A SUBSTRATE

The invention relates to a process and a device for scanning a surface of a shaped substrate, the said scan particularly allowing the detection of local defects and the three-dimensional measurement of the shape of a substrate having a reflective surface.

Although not limited to such applications, the invention will be more particularly described with reference to scanning of the surface of windows and even more specifically to the scanning of curved windows intended for the automotive industry.

Current specifications by vehicle manufacturers are encouraging the glass industry to realize laminated side windows constituted, in particular, by two panes of glass of reduced thickness compared with a toughened monolithic window. The realization of such panes of glass of reduced thickness is delicate and can lead to surface defects. These defects can become very troublesome after assembly to form a laminated window, since they lead to optical distortion phenomena, accentuated owing to the connection to a second pane of glass, and also to delamination problems. The presence of such optical defects generally results in the windows being rejected, since they are unacceptable. The windows being already laminated, they are difficult to recycle and the costs of production become unacceptable.

There is therefore a desire to proceed to detect such defects as early as possible in the production chain and particularly prior to realizing the assembly of a laminated window.

The methods which are normally used consist in observing the laminated window in terms of transmission or reflection according to standardized methods, such as by visual observation outside the production line and after the assembly of the laminated window. As previously explained, such a check is too late and has an adverse effect upon production costs.

In addition, industrial methods exist for checking a reflective surface, by which surface defects can be detected by reflection measurements of the reflection of a regular design. These methods are shown to be limited in terms of their applications and the reliability of their results. Indeed, in the case, particularly, of curved windows, these types of scanning methods display weaknesses owing, in particular, to the adopted principle for the reflection measurement.

Apart from the defects, it is worth making sure that the geometry of the window conforms to that which is desired or at least falls within a fixed envelope of tolerance. The checking method is mechanical; sensors take punctual measurements so as to compare them to those of a template consistent with the idle time. Now, this method constitutes a labour cost, in particular for the positioning of the sensors relative to each new window geometry to be checked, as well as a cost of supplies for the measurements, particularly the need for a distinct template for each window geometry, costs in which a reduction would be increasingly welcome.

The inventors have thus set themselves the task of designing a method for scanning a surface, particularly a reflective surface, which does not have the drawbacks of the methods previously stated and, in particular, by which a reflective surface of a shaped substrate can be scanned in a precise and repetitive manner and by which, in particular, the costs of checking the consistency of windows on a production line are reduced.

This object has been achieved according to the invention by the use of a process for scanning a surface of a substrate, which process consists in taking at least one reflected image of at least one test pattern on the said surface and extracting by digital processing local phases in two directions, characterized in that variations in local slopes are calculated by digital processing from the local phases in order to deduce therefrom variations in curvature or variations in altitude of the said surface.

Thus, a first type of surface scan leads from the phase extraction to the resultant deduction of variations in local slopes, which variations, by means of a calculation by derivation, allow variations in local curvatures to be defined. Such a scan allows the presence of defects on the surface of a substrate to be determined.

A second type of surface scan leads from the phase extraction to the resultant deduction of variations in local slopes, which variations, by means of a calculation by integration, allow altitude deviations to be defined in order to establish the variation in overall three-dimensional shape of the substrate.

The image is taken reflected on a reflective surface.

It is important that the test pattern or test patterns, a plurality being able to be used in the case of a complex surface, should be reflected over the whole of the surface of the substrate. Preferably, the reflected image is taken instantaneously.

The scanning method according to the invention envisages the adoption of a test pattern, the design of which can be deformed, whereby an image of the said test pattern can be obtained which is substantially less distorted than that of an ordinary test pattern owing to the curvature of a substrate when a rounded substrate is scanned. The invention can thus advantageously be applied to the scanning of rounded substrates, such as curved windows. The scan being usually effected on the convex surface of such curved windows, the process according to the invention envisages the use of a test pattern, the size of which is dictated by that of the window, bearing in mind that the captured image is that of the test pattern on a convex surface.

According to one embodiment of the invention, a real or physical test pattern is envisaged, the size of which, as previously stated, is dictated by the size of the substrate and more particularly by its shape. Such a test pattern is more particularly suitable for taking an image on reflective surfaces.

According to another embodiment of the invention, a virtual test pattern is used; this is constituted in this case, for example, by a projected test pattern, the image of which is preferably taken reflected on the substrate.

A preferred embodiment of the invention consists in using a flat test pattern, the design of which is deformed. Another embodiment envisages a rounded test pattern; in this latter case, the design, which would be non-deformed if the test pattern were flat, is once again deformed such as envisaged by the invention. It is further possible to envisage a combination of these two embodiments, by realizing a rounded test pattern comprising a design which would already be deformed if the test pattern were flat.

According to a first embodiment of the invention, the test pattern is designed such as to compensate rigorously for the curvature of the scanned substrate. Such an embodiment is industrially conceivable in the case of a scanning of identical substrates. Yet particularly in the case of curved windows intended for fitting in automotive vehicles, the production series relate to limited numbers of windows, whereas the number of windows which are different, and hence possess different curvatures, is very large.

According to a second embodiment, the inventors thus envisage a deformation of the design of the test pattern compatible with the scanning of several models of substrates having different curvatures. Tests have shown that the choice of a deformation of the design which does not allow strict compensation of the rounding of the substrate yielded precise and reliable scanning results; indeed, the deformation of the design of the test pattern according to the invention allows the at least partial compensation of the deformation of the image taken on the shaped substrate and thus allows satisfactory scanning in the zones of curvature and better scanning of the peripheral zones of the substrate.

An advantageous realization of the invention envisages scanning of the substrate in dynamic state, that is to say in motion or in the course of deformation.

According to one embodiment of this realization, the scanning is effected on a substrate moving past on a conveyor. Compared with methods which require the substrate to be immobilized, the invention has the advantage of being able to be used to scan moving substrates. It therefore additionally offers an advantage in terms of productivity and production costs, owing to the speed of its execution.

In order to ensure the reproducibility of the scan, the substrate in travel on a conveyor is advantageously placed by mechanical positioning means in a position suitable for facilitating the digital processing, in particular for best realizing a comparison of the reflected image of the test pattern with a reference test pattern. Also, prior to carrying out the scan, the passing substrates are positioned identically in the two directions of the plane formed by the conveyor.

The processing of the image according to the invention comprises several stages, in particular a stage of superimposing the reflected image of the test pattern onto a reference test pattern in such a way as to obtain a moiré, the phase extraction stage being realized, for example, according to a "phase stepping" method. This method is described in the article "Design of algorithms for phase measurements by the use of phase stepping", signed by Yves Surrel and published in Applied Optics Vol. 35, No. 1, dated 1 Jan. 1996.

Compared with other processing methods, of the Fourier transform type, such image processing operations according to the invention yield, in particular, precise and repetitive scanning results for the whole of the surface of the substrate. Indeed, the other image-processing methods, particularly using Fourier transform, lead to unsatisfactory results for the peripheral zones of the substrate.

The stage following the extraction of local phases consists in comparing these phases to reference phases, deducing therefrom phase variations and correcting these phase variations through the use of a sensitivity factor s, which is heavily dependent upon the observation conditions and the measurement tools used, such as to calculate the variations in local slopes.

The scan which is thus obtained according to the invention allows, in particular, a check to be made of the surface state of a substrate and, in addition, an overall scan to be made which allows measurement of the rounding of the substrate, that is to say the variation in three-dimensional shape of the substrate.

The process thus described according to the invention allows the productivity and production costs of, in particular, curved windows to be further improved; indeed, the current requirements in relation to curving within the automotive industry are very demanding and call for rigorous checking. The methods currently used generally call for an off-line checking apparatus. The apparatuses allow either a checking of the periphery or, increasingly, a checking of the whole of the surface, required in order to meet the aesthetic requirements. The necessary apparatuses are therefore either mechanical sensors, which have a not insignificant cost, or a three-dimensional checking machine, in the most demanding cases, which makes use of a marble. In this latter case, the apparatus is dedicated to a single type of window and gives rise to a very considerable cost; in addition, the measurement times are very long.

It is evident that the process according to the invention yields satisfactory results at reduced costs and allows much more rapid checking. This latter advantage is considerable, since, should a defect or non-fulfillment of the required rounding become apparent, it will allow rapid intervention in the production process. Such intervention will allow, on the one hand, the quantity of defective products, and hence material losses, to be limited and will consequently allow an improvement in both production rates and productivity.

Compared with customary methods, the scanning process according to the invention, which allows the rounding to be checked, also has the advantage of carrying out a scan without contact and without any preparation of pre-treatment of the surface to be scanned. That procures a certain advantage in the production of a thin glass pane, that is to say having a thickness less than 2.5 mm. Indeed, such panes of glass are very sensitive to contact throughout the production phase and, if subjected to a contact, can find their rounding damaged during the checking.

This process can equally well be applied to the checking of the rounding for toughened monolithic glasses, such as for the side windows or backlights of vehicles.

The invention has a further advantage in the checking of thin glass panes; these thin glass panes can be intended, for example, for fitting in automotive vehicles to form side windows. For this type of use, the thin glass panes are put together in pairs using a plastics film, made of polyvinyl butyral (PVB) for example, to form a laminated window. The scanning process according to the invention, which consists in obtaining an image of a glass pane, will allow the quality of the laminated window to be predicted through the use of mathematical modelling and, in particular, numerical calculation; indeed, the knowledge according to the process of the image of two panes of glass intended to be put together to form a laminated window will yield information regarding the optical quality of the laminated window. The process according to the invention thus allows laminated windows which are unacceptable in terms of their optical quality to be detected prior to their assembly. Amongst other advantages, the invention thus prevents all recycling problems arising from the presence of two materials and it further improves, of course, the productivity of the production process for such laminated windows.

According to another, dynamic state embodiment, the scanning process according to the invention is effected on a substrate in the course of deformation. According to such an application of the process according to the invention, it is possible to check the rounding of the substrate during the course of its deformation.

When a glass pane is curved, for example, instantaneous scans of the type permitted by the invention, successively repeated, will allow the deformation of the window to be checked. More particularly, should complex shapes be sought, such scans will allow the process used to be optimized; in these cases, indeed, the curving processes which are used can be realized in several stages and the knowledge of the deformation of the window during the process can thus allow the moment of passage from one stage to another to be optimized. The knowledge of the deformation can further allow the improved use of heating means during one or other of the stages.

Still in the case of the rounding of a substrate being checked in the course of its deformation, the invention advantageously envisages this checking being carried out with reference to the concave face of the substrate, in particular when the said substrate is supported by mechanical tools during its deformation, for example by frames or rollers in the case of windows. Preferably, when conditions allow, the scan according to the invention will be carried out on the convex face of the substrate.

The invention likewise proposes a device for realizing the process according to the invention.

The device according to the invention comprises at least one camera, a flash-type pulse lighting, digital image-processing means and at least one test pattern, the projection of which covers the whole of the surface of the substrate, the design of the test pattern being able to be deformed in at least one direction.

The camera is advantageously a digital camera; such a camera allows the digitalization to be made at the level of the CCD pick-up. That has the advantage that no analogue signal is transported by cables within which it can be damaged and, furthermore, deteriorations in the signal due to an analogue/digital conversion are likewise avoided.

The pulse-type lighting is envisaged and is suitable for obtaining a clear image of the substrate in travel or in the course of deformation; advantageously, a laser or laser diode type lighting is used. The luminosity is chosen, moreover, so as to illuminate the whole of the surface of the test pattern in a homogeneous manner.

The digital processing means are fit to generate a moiré and comprise algorithms for phase extraction calculation, for conversion calculation and for derivation or integration calculation.

The device according to the invention, when it relates to the scanning of a moving substrate, is advantageously used above a conveyor. This conveyor is preferably designed to offer a dark surface and thus to enhance the contrast of the image captured by the camera; the conveyor is constituted, for example, by a belt conveyor, of the carpet type, the colour of which is advantageously dark and preferably black.

The conveyor has a very precise inherent flatness in order to define a precise supporting plane for the substrate to be measured.

According to a preferred embodiment of the invention in the case of a substrate moving past on a conveyor, the camera is placed above the test pattern.

Preferably, also, the optical axis of the camera lens is normal to the surface of the substrate at the centre of the field of observation when a single test pattern is used; in other words, the direction of observation of the camera is normal to the surface of the substrate at the centre of the field of observation. According to such an embodiment and in the case of a virtual test pattern, the optical axis of the projector is parallel and close to the optical axis of the camera.

Before the scanning station, mechanical positioning means are advantageously provided on the conveyor, which allow the substrate to be positioned in the two directions formed by the plane of the conveyor in a position suitable for facilitating the digital processing. These means are all means known to the person skilled in the art, for example systems of limit stops and/or guide rails.

The device according to the invention, when it relates to the scanning of a substrate in the course of deformation, is advantageously placed in a warm chamber, for example in the case of the curving of a window realized in just such a warm chamber. According to other processes for the curving of windows, the device is used at ambient temperature.

The device thus described according to the invention can therefore be used to scan a surface, particularly a reflective surface, of a substrate, which is in particular shaped and preferably transparent.

The invention first of all allows the state of such a surface to be checked and hence the defects to be scanned. In the case of windows, for example, such a check can thus allow the origin of the defects to be understood and for these to be remedied by appropriate action upon the device or upon the production or forming process.

Where laminated windows are realized, moreover, the scanning of the surface of each of the monolithic windows will allow the optical quality of the laminated window to be predicted. The operation corresponds in this case to a numerical calculation based on the two images obtained and to an appropriate statistical processing.

The invention can additionally allow measurement of the variation in overall three-dimensional shape of a shaped substrate. The scan, which can be made in dynamic state, allows either the shape of the obtained substrate to be checked or the evolution of the shape to be checked when the scan is done in the course of deformation.

The invention can also allow the inherent flatness of a substrate to be measured. Indeed, the knowledge of the scan according to the invention made of the surface of the substrate, which brings defects to light and yields its three-dimensional configuration, allows the inherent flatness of the said substrate to be checked for applications of flat substrates. Such checking of the inherent flatness is, for example, useful for window applications, for example in the building trade field. This checking of the inherent flatness becomes very important for other applications of windows, in particular in the field of visual display screens. Indeed, for this type of application, the inherent flatness must be very strict, in particular in order to satisfy the manipulations to which the window is subjected during all the treatments effected for the purpose of realizing a screen; in order to prevent it being damaged during manipulations for leading the window from one treatment to another, the said window is transported by suction devices which limit the contacts and the assaults of tools on the glass. Manipulations of this type by the use of suction call for a perfect inherent flatness of the window in order to prevent any risk of fall of the transported window.

The above-stated visual display screens are all types of screens which have to be subjected to treatments such as coating applications, engravings, etc. and are, for example, plasma screens, field emission displays (FED), micropoint screens. A checking of the inherent flatness of a window can likewise be sought for the realization of vacuum windows or flat lamps, for which a limited and regular space is sought between two glass panes.

It is evident that, for these different applications, the knowledge of the inherent flatness of a glass pane or window can allow a defective product to be scrapped before it is actually used in the make-up of the final product and thus leads to a considerable reduction in production costs by enhancing the production yields in the final stages of development of these products.

In addition, where substrates are transported by suction, wherein falls of the windows are able to block a production line, the prior scrapping of substrates not offering sufficient inherent flatness to satisfy the process brings improved productivity.

A final advantage of the scanning method according to the invention for checking the inherent flatness of a substrate is that, as in the preceding cases, it can be carried out rapidly and, moreover, on substrates in travel, for example on a conveyor, and therefore without risk of lowering the production rates.

Other details and advantageous characteristics of the invention will emerge below from the description of illustrative embodiments of the invention with reference to FIGS. 1 and 2, in which FIG. 1 shows a diagram illustrating the scanning principle.

Figure 2:
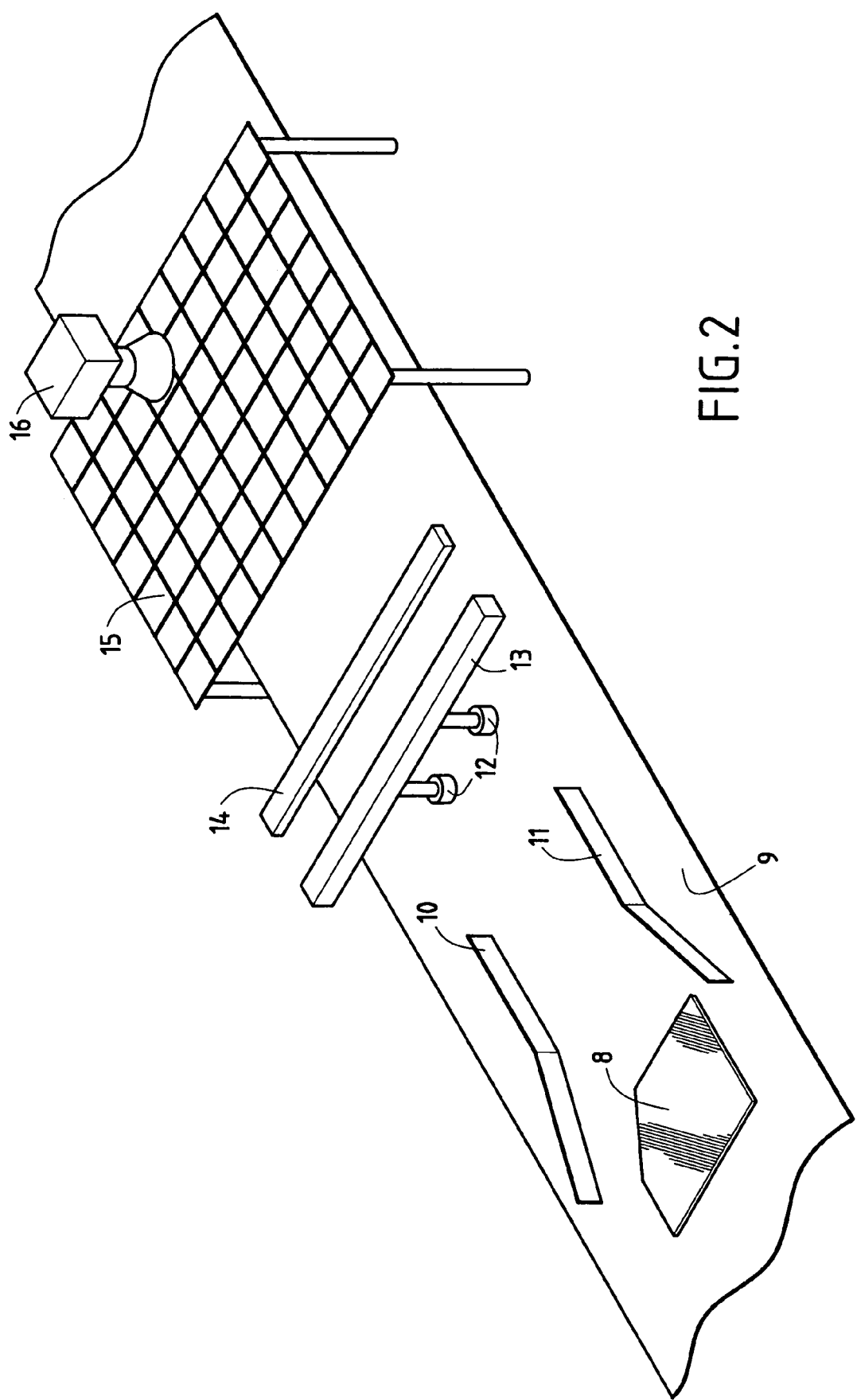

FIG. 2 shows a diagram representing an application of the invention for checking window glazing.

The figures are not represented to scale in order to make them easier to understand.

FIG. 1 represents a device illustrating the measurement principle according to the invention, resulting in an instantaneous image being taken of a test pattern 1 reflected on a substrate 2. The image of the test pattern is, as previously stated, advantageously obtained with the aid of a CCD camera 3 in order to avoid all risks of damage to the captured signal. The test pattern 1 used is advantageously a flat, physical test pattern, the design of which can, for example, be deformed in that it contains shaped lines.

The instantaneous image is advantageously obtained by the use of a flash-type lighting system 4; this is constituted, for example, by a laser diode.

The test pattern 1 according to the invention, particularly where a curved substrate 2 is scanned, has a design which is deformed such that the image of the test pattern captured in reflection on the said substrate displays quasi-parallel lines, these being strictly parallel given that the deformation of the design of the test pattern compensates for the rounding of the substrate. As previously stated, a deformation of the test pattern design is advantageously chosen which will produce satisfactory results in terms of scans for a range of substrates having different curvatures.

Moreover, the measurement is preferably realized on the convex face of the substrate, particularly in order to obtain a better contrast, and consequently calls for a test pattern of relatively large size such that its reflected image covers the whole of the surface of the substrate to enable the whole of the surface to be scanned.

The image captured by the camera 3 is transmitted to a computer 5 in order to be processed, in a number of stages, by digital processing means.

First of all, the image of the reflected test pattern taken by the camera is digitalized, it is superimposed onto a reference test pattern to form a moiré, the reference test pattern being able, for example, to be constituted by the pixels of the camera. To each pixel of the digitalized image is attached an elementary area of the surface of the substrate. Starting from the moiré and using an algorithm for calculation according to the "phase stepping" method, for example, a map is extracted of the local phases relating to the elementary areas of the surface of the substrate. Next, the local phases are compared to memorized reference phases deriving from a measurement of a reference sample or from a calculation produced by CAD (computer-aided design), in order to deliver phase variations. From the phase variations, the variations in slopes are calculated by means of a sensitivity factor s, which is heavily dependent upon the observation conditions and the measurement tools used.

The variations in local slopes are next used in a calculation by derivation algorithm or in a calculation by integration algorithm in order respectively to show the presence of surface defects 6, 7, the knowledge of which is obtained precisely in two directions, or to measure the variation in three-dimensional shape of the substrate.

In the case of a flat substrate, it is similarly possible to check the inherent flatness of the entirety of the surface of the said substrate.

FIG. 2 represents a diagram of an installation which allows a scan according to the invention of the surface of a window 8 in travel on a conveyor 9. The window 8 which arrives on the conveyor is first of all reorientated in a direction perpendicular to its direction of advancement on the conveyor 9, with the aid of two guides 10, 11. These guides 10, 11 will allow the window 8 to be orientated in the desired direction, the latter having already possessed an approximate orientation imposed when it was deposited onto the conveyor. The trajectory of the window 8 is next interrupted by two limit stops 12 supported by an arm 13, the position of which can be altered in a vertical direction. When the window 8 comes into contact with a first limit stop 12, it is blocked at this point and the conveyor causes the said window to pivot until it comes into contact with the second limit stop 12; the window then finds itself reorientated, in its direction of advancement, in a predefined position suitable for best effecting the comparison of the reflected image of the screen pattern with the reference screen pattern. The device for lifting the arm 13 is next actuated such that the limit stops 12 no longer obstruct the passage of the window 8, which thus continues its travel on the conveyor 9. The device for lifting the arm 13 is advantageously actuated automatically as soon as the window 8 is in contact with the two limit stops 12. Moreover, the ascent of the limit stops 12 is designed to be very quick such that it does not risk damaging the window 8, which has its convex surface upwards and is therefore higher in its centre than on the edge which was in contact with the limit stops 12. The properly positioned window 8 then passes under a detector 14, for example an optical detector, which will determine the moment of triggering of the flash attached to the capture of an image of the window 8.

This triggering of the flash occurs as soon as the window 8 is located beneath the test pattern 15, such that the image captured by the camera 16 of the test pattern 15 reflected on the window covers the entirety of the convex surface of the said window 8.

The captured signal is next transmitted to a computer, in which it is processed according to the algorithms for "phase stepping", conversion and derivation or integration calculation.

Thus, the scanning method of the invention allows large surfaces of $m^2$ proportions, such as a window, to be scanned in dynamic state and with very good resolution in the order of 10 µm.

The results obtained lead to possible detection of the defects or to a knowledge of the rounding of the window. This information can then be used to intervene in stages in the window production process and to remedy the defects. In other cases and particularly for the realization of laminated windows, the results allow the quality of the window to be known in advance and possibly for the window not to be made if the optical properties are not satisfactory.

In the case of a window-curving process, the results obtained according to the invention in the course of realization of a curved window will allow better monitoring of the process and improvement of the production yield.

Where the inherent flatness of a window, intended for the realization of a visual display screen, is checked, the results obtained according to the invention will also bring about improved rates of production of the said screens, in that those windows whose inherent flatness is not satisfactory are scrapped before they find themselves on the production lines for these screens.

The device described above has been adopted by way of example, but the tools used can be more numerous, for example several cameras and test patterns, in particular where it is a case of scanning complex shapes having, for example, different curvatures. These will be studied using several reflected images of a plurality of test patterns recorded by several cameras, the whole of the surface of the substrate having to be covered by reflected test patterns.

The invention claimed is:

1. Process for scanning a surface of a substrate, comprising:
   projecting light onto a reflective surface having a test pattern formed thereon;
   directing reflected light including a test pattern image of the test pattern that is reflected from the reflective surface onto the surface of the substrate;
   capturing a reflected image of the test pattern image that is reflected from the surface of the substrate when the substrate is in a dynamic state;
   extracting by a phase stepping process local phases in two directions from the captured reflected image; and
   determining optical properties of the surface of the substrate by calculating variations in local slopes by digital processing from the local phases, the extracted local phases being compared to reference phases for deducing phase variations which are converted by a sensitivity factor to form variations in local slopes, and to deduce, from said variations in local slopes, variations in curvature by a digital processing involving derivation or variations in altitude of the surface of the substrate by a digital processing involving integration.

2. Process for scanning a surface of a substrate according to claim 1, wherein the digital processing comprises superimposing the reflected image of the test pattern image onto a reference test pattern to obtain a moire from which the extracting of the local phases is realized.

3. Process for scanning a surface of a substrate according to claim 1, further comprising placing the substrate in a position suitable for facilitating the digital processing.

4. Process for scanning a surface of a substrate according to claim 3, wherein the substrate is placed by a mechanical positioning device.

5. Process for scanning a surface of a substrate according to claim 1, wherein the substrate upon which the reflected light including the test pattern image is directed is a transparent substrate.

6. Process for scanning a surface of a substrate according to claim 1, further comprising deforming the surface of the substrate, and wherein the capturing of the reflected image is performed during the deformation of the surface of the substrate.

7. Process for scanning a surface of a substrate according to claim 1, wherein the at least one test pattern is reflected over a whole of a surface of the substrate.

8. Process for scanning a surface of a substrate according to claim 1, wherein the one reflected image is taken instantaneously.

9. Process for scanning a surface of a substrate according to claim 1, wherein a design of the test pattern is deformed in at least one direction.

10. Device for realizing the process according to claim 1, comprising at least one camera configured to capture the reflected image, at least one flash-type pulse lighting configured to project the light onto the reflective surface, at least one test pattern, and digital image-processing means, wherein the processing means are configured to generate a moiré.

11. Device according to claim 10, wherein the digital image-processing means comprises algorithms for phase extraction calculation, for conversion calculation, and for derivation or integration calculation.

12. Device according to claim 10, wherein the camera is positioned above a conveyor.

13. Device according to claim 12, further comprising mechanical means provided for focusing the substrate in two directions forming a plane of the conveyor.

14. Device according to claim 10, wherein the device is positioned within a warm chamber.

15. Device according to claim 10, wherein an optical axis of a lens of the camera is normal to a surface of the substrate at a center of a field of observation when a single test pattern is used.

16. Use of a device according to claim 10 for scanning defects of a window.

17. Use of a device according to claim 10 for measuring a variation in overall three-dimensional shape of a window.

18. Use of a device according to claim 10 for checking inherent flatness of a window.

19. Use of a device according to claim 10, for checking a window intended for realizing a visual display screen.

20. Process for scanning a surface of a substrate according to claim 1, further comprising:
   deforming a test pattern based upon a curvature of the substrate.

21. Process for scanning a surface of a substrate, comprising:
   directing light including a test pattern image of a test pattern onto the surface of the substrate, wherein the substrate is a transparent substrate;
   capturing a reflected image of the test pattern image that is reflected from the surface of the transparent substrate;
   extracting by a phase stepping process local phases in two directions from the captured reflected image; and
   determining optical properties of the surface of the transparent substrate by calculating variations in local slopes by digital processing from the local phases, the extracted local phases being compared to reference phases for deducing phase variations which are converted by a sensitivity factor to form variations in local slopes, and to deduce, from said variations in local slopes, variations in curvature by a digital processing involving derivation or variations in altitude of the surface of the transparent substrate by a digital processing involving integration.

22. Process for scanning a surface of a substrate according to claim 1, wherein the capturing of the reflected image is performed while the substrate is being transported.

23. Process for scanning a surface of a substrate according to claim 22, wherein the capturing of the reflected image is performed while the substrate is being transported on a conveyor and the substrate is focused in two directions forming a plane of the conveyor.

24. Process for scanning a surface of a substrate according to claim 21, further comprising:
   deforming a test pattern based upon a curvature of the substrate.

25. Process for scanning a surface of a substrate, comprising:
   directing light including a test pattern image of a test pattern onto the surface of the substrate;
   deforming the surface of the substrate;
   capturing a reflected image of the test pattern image that is reflected from the surface of the substrate while the surface of the substrate is being deformed;
   extracting by a phase stepping process local phases in two directions from the captured reflected image; and
   determining rounding of the surface of the substrate by calculating variations in local slopes by digital processing from the local phases, the extracted local phases being compared to reference phases for deducing phase variations which are converted by a sensitivity factor to form variations in local slopes, and to deduce, from said variations in local slopes, variations in curvature by a digital processing involving derivation or variations in altitude of the surface of the substrate by a digital processing involving integration.

26. Process for scanning a surface of a substrate according to claim 25, further comprising:

deforming a test pattern based upon a curvature of the substrate.

\* \* \* \* \*